United States Patent [19]

de Estrada

[11] Patent Number: 4,722,685
[45] Date of Patent: Feb. 2, 1988

[54] TOOL FOR ADAPTING A PORTABLE LATHE TO TREAT THE BACK MOLAR TEETH OF HORSES

[76] Inventor: Juan M. de Estrada, Las Heras 3737, (1425) Buenos Aires, Argentina

[21] Appl. No.: 866,344

[22] Filed: May 23, 1986

[30] Foreign Application Priority Data

May 30, 1985 [AR] Argentina ............................ 300568

[51] Int. Cl.$^4$ .............................................. A61C 1/10
[52] U.S. Cl. ...................................... 433/1; 433/114; 433/116
[58] Field of Search .................... 453/116, 114, 1, 165, 453/166

[56] References Cited

U.S. PATENT DOCUMENTS 1,562,110  11/1925  Mash .................................... 433/112
2,176,339  10/1939  Henneman .......................... 433/116

FOREIGN PATENT DOCUMENTS 2637915  3/1978  Fed. Rep. of Germany .......... 433/1

Primary Examiner—Robert Peshock
Attorney, Agent, or Firm—Zarley, McKee, Thomte, Voorhees & Sease

[57] ABSTRACT

A dental tool for grinding spikes formed on the molar teeth of horses. An elongated hollow tube is fixed to the tool grip, and the grinding bur is removably attached at the other end of the tube to a rotary flexible connector that passes along inside the tube. The length of the tube is approximately the mean depth of a horse's mouth, to enable the tool to access teeth lying well back in the mouth. A detachable cover is provided for the bur, having an opening for exposing the bur to the tooth under treatment and protecting the tongue and cheek tissue from possible injury.

6 Claims, 2 Drawing Figures

U.S. Patent  Feb. 2, 1988  4,722,685
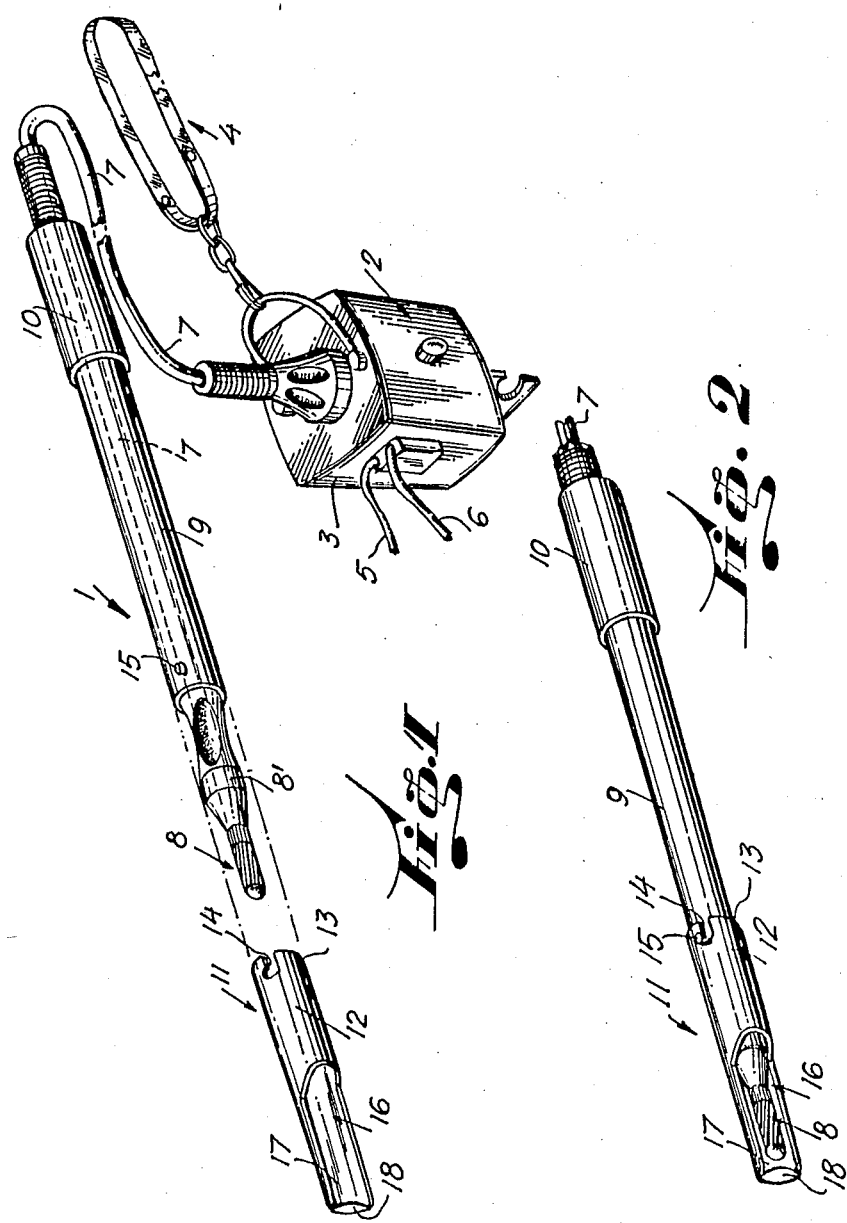

TOOL FOR ADAPTING A PORTABLE LATHE TO TREAT THE BACK MOLAR TEETH OF HORSES

BACKGROUND OF THE INVENTION

The present invention relates to a dental lathe having a portable grinding tool for use with animals, and particularly, with equines.

The dental pieces of many animals must be treated or corrected odontologically in order to prevent or alleviate a number of nutritional and other relates problems.

In practice, sharp edges and spikes commonly develop in the dental pieces of horses, mainly in the upper maxillary. Sharp edges develop at the mount faces thereof at the level of the molars, due to uneven abrasion of the mastication surfaces and to the anatomic shaping of the maxillaries. Since the upper maxillary is wider than the lower maxillary, this causes the formation of these sharp edges. Furthermore, because the teeth of this animal species grow in a generally slanted direction, the top teeth growing down and outwards and the bottom teeth up and inwards, such sharp edges or spikes also project sidewardly. These sharp edges may injure the mucosa of the cheeks.

Regarding the lower maxillary, edges develop at the tongue face of the molars, which may injure the tongue mucosa. These sharp edges and spikes prevent normal mastication by the animal, which, besides originating nutritional problems, also adversely affect the performance of otherwise active animals due to the pain caused thereby.

The above mentioned nutritional problems also impair the efficiency of animals in sport activities, e.g. polo ponies, as well as in stallions and mares involved in reproduction.

These dental alterations, which are usual in equines, result in terminal pathologies, such as "colics" of different types which occur by defective mastication, and a poor disintegration of the foods to be ingested. Congenital or acquired pathologies, such as "stepped" teeth, "sheared" teeth, or other types of uneven growth of teeth, may also be found.

DESCRIPTION OF THE PRIOR ART

At present, a long file is used for levelling the molars, requiring a cumbersome operation by the operator, which causes pains and disturbances to the animal. The results obtained do not generally justify using this method.

Another system general used consists in bashing the irregularities with a heavy hammer, which, although quicker, is more painful, less precise and may even be dangerous sometimes.

A grinding tool is known outside the odontological domain, consisting of a hand-held rotary bur connected by a flexible rotary capable to the shaft of an electric motor, used for levelling the hoofs of horses and for forming the slots, scores or tips that are required to correct some pathologies of the third phalanx, such as the chronic abnormal growth of the hoof into the leg, or in fractures of the hoof front, for which treatment such slots or scores are specified. This tool is also used for rounding off the horn ends of horned animals and for levelling the foot of cloven-hoofed animals.

However, because the back molar teeth in some animal species such as equines are rather set back in the mouth, they may not readily be accessed with this tool, without having to shove tool and hand into the mouth, which is rather inconvenient generally and downright impossible in some cases. Furthermore, the use of a mechanical abrasive tool inside a cavity imperils other, soft tissue, parts thereof.

BRIEF DESCRIPTION OF THE PRESENT INVENTION

In accordance with the present invention, the hand-held tool includes an elongated spacer which separates bur and grip a distance equivalent to the depth of the mouth. Hence, just a minimum of parts need be put in the mouth for carrying out a back molar grinding operation, increasing tool maneuverability and lessening animal distress. The elongated spacer is made from a tube through which the flexible cable passes to connect the bur to the output shaft of a motor. This way, a handy and efficient dental lathe is provided for in accordance with the present invention.

The portable grinding tool may be used for blunting the first premolar which injures the mucosa of the cheeks, causing wide and deep erosions, when the cheeks are pressed against the sharp points of the first premolar, for example, by the lifting bridle usually used in polo ponies.

The portable grinding tool may be also used for removing the "capsules" which form when the second or third deciduous premolar remain retained. The portable grinding tool may be further used for levelling the incisives in cases of excessive or undue growth, and for removing odontological sarcomas.

The main advantages of the portable grinding tool of the present invention is the speed and quality of operation. The portable grinding tool is further provided with a protective hood that allows the apparatus to be well located within the mouth of the animal and prevents the grinding bur from injuring the mucosa, tongue, palate or gums of the animal, especially because of the power needed for abrading the dental pieces of equines. The protective hood is further designed to prevent folds of the mucosa from being caught between the grinding bur and the hood or the tip of the grinding bur coming into contact with soft areas of the mouth.

BRIEF DESCRIPTION OF THE DRAWINGS

FIG. 1 is a perspective view of the dental lathe of the present invention, and

FIG. 2 shows a partial perspective view of the assembled portable grinding tool of the present invention.

In both figures, same reference numbers indicate same or corresponding parts.

DETAILED DESCRIPTION OF THE PREFERRED EMBODIMENT

As shown in the drawings, reference number 1 indicates generally the portable grinding tool, which includes an electric motor 2 of appropriate characteristics that is housed within a suitably insulated frame 3. Frame 3 is provided with a collar 4 for hanging the lathe from the neck of the operator. The electric motor 2 may be a ¼ HP and 16,000 r.p.m. motor, and is provided with an electrical cable 5 of suitable length with a plug for plugging into a 110 VAC electric supply, and with an electrical cable 6 for an on-off push button switch (not illustrated).

A long mechanical flexible cable 7 is connected to the output shaft of the electric motor 2. This rotary connector cable 7 transmits grinding rotation to an interchangeable grinding bur 8 attached to one end of an elongated spacer tube 9, opposite a hand grip tube 10 made of rubber or a similar material. The spacer 9 is made from a stainless steel cylindrical tube about 12" long, ¾" in diameter and 1/16" wall thickness. The 12" length is obtained from the average depth of a horse's mouth. The grinding bur 8 may be the R-12 model manufactured by DUX having a ⅛" diameter, and is removably attached from its bur holder 8' which in turn is pressure fixed inside the distal end of tube 7 and held in place with an epoxy adhesive.

The hand-tool 1 is provided with a protective hood 11 in relation with the grinding bur 8. Hood 11 comprises a detachable cap 12 with a coupling section 13 at the proximal end thereof comprising a recess 14 which, together with a pin 15 on tube 11, forms a bayonet type coupling. The cap 12 is made from a stainless steel tube, ⅞" in diameter, 1/16" wall thickness and slightly over 5" long. In order to allow the grinding bur 8 to carry out its specific function, cap 12 has an approximately 180° wide side window 16, which is open against a tube projection 17 that terminates in a lug 18 for protecting the animal mucosas against injures, as mentioned hereinbefore. The distal end projection 17 of the hood 11 is terminated by bending inwardly the tip thereof to form the lug.

Although the essential features of the present invention have been brought out by means of the illustrated preferred embodiment, the invention is not limited thereto, rather it depends to all alternate forms within the purview of the following claims.

I claim:

1. A dental lathe for use with animal species and comprising:

a motor having a rotary output shaft, a hand-tool having a grip for manipulating the hand-tool and a bur for grinding tooth irregularities of an animal, and a flexible rotary connector for transmitting rotational movement from said motor shaft to said bur;

wherein said hand-tool further includes means for adapting said dental lathe to enable said bur to be adequately applied to the back molar teeth of a predetermined animal species, said adapting means comprising:

a hollow elongated spacer separating said bur and said grip a predetermined distance in accordance with the average depth of the mouth of said animal species, to enable said bur to reach said back teeth whilst said grip is held outside said mouth, and a protector device for covering part of said bur to avoid other parts of said mouth, such as inner cheek or tongue, coming into contact with said bur; said protector device comprising:

a hood having a generally closed tip for providing greater protection to said mouth, and a partially open side for exposing said bur to said tooth irregularities.

2. The dental lathe of claim 1, wherein said bur is removably attachable to one end of said flexible connector, and part of said flexible connector extends inside said hollow spacer.

3. The dental lathe of claim 1, wherein said protector device is removably attachable to the bur end of said elongated spacer.

4. The dental lathe of claim 1, wherein said hood is a hollow cylindrical hood having means for attaching said protector device to said hand-tool.

5. The dental lathe of claim 4, wherein said open side is longer than said bur and sustains an arc of approximately 180° of said cylindrical tube.

6. The dental lathe of claim 1, wherein said animal species is equines, and said spacer is at least approximately 12 inches long.

* * * * *